United States Patent
Casellas

(10) Patent No.: US 10,787,429 B1
(45) Date of Patent: *Sep. 29, 2020

(54) PRODUCTS AND METHODS OF MECHANICAL EXTRACTION AND PURIFICATION OF TETRAHYDROCANNABINOLIC ACID

(71) Applicant: Eco Green Grow Holdings, LLC, Denver, CO (US)

(72) Inventor: Julian Casellas, Longmont, CO (US)

(73) Assignee: Eco Green Glow Holdings, LLC, Denver, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/556,128

(22) Filed: Aug. 29, 2019

Related U.S. Application Data

(63) Continuation of application No. 16/449,304, filed on Jun. 21, 2019.

(60) Provisional application No. 62/856,837, filed on Jun. 4, 2019.

(51) Int. Cl.
  *C07D 311/80* (2006.01)
  *A61K 36/185* (2006.01)
(52) U.S. Cl.
  CPC ................. *C07D 311/80* (2013.01)
(58) Field of Classification Search
  None
  See application file for complete search history.

(56) References Cited

U.S. PATENT DOCUMENTS 9,066,910 B2 * 6/2015 Rosenblatt ........... A61K 36/185

OTHER PUBLICATIONS

U.S. Appl. No. 16/449,304, filed Jun. 2019, Casellas, Julian.*
Coddington, H., The Physics Behind Rosin: Heat & Pressure, Pure Pressure, pp. 1-13. (Year: 2017).*
Alchimia, "How to make THCA Crystals & Solventless Sauce," Alchimia Blog: News about marijuana and growing guide, pp. 1-10. ( Year: 2018).*
"What Is Bubble Hash?" mmjdoctoronline, pp. 1-12. (Year: 2017).*

* cited by examiner

*Primary Examiner* — Michael Barker
(74) *Attorney, Agent, or Firm* — Kevin Fortin

(57) ABSTRACT

A method for manufacturing high-purity tetrahydrocannabinolic acid. The method includes providing *Cannabis sativa l.* biomass, mechanically separating trichomes into phytochemical mixture including tetrahydrocannabinolic acid, drying the phytochemical mixture, creating a first press product by pressing the dried phytochemical mixture through a mesh screen with a pressure within the range of 5-120 psi and at a first temperature between 90-120° F. The first press product is aged to naturally release acid form cannabinoids from terpenes, undesirable lipids, and chlorophyll. Second pressing the aged first press product at gradually increasing temperatures to release the undesirable lipids and chlorophyll to create a second press product. In a third press increasing the temperature to beyond the melting point, and below the boiling point of tetrahydrocannabinolic acid to yield high-purity tetrahydrocannabinolic acid having a 90-99.99% purity.

15 Claims, 2 Drawing Sheets

PRODUCTS AND METHODS OF MECHANICAL EXTRACTION AND PURIFICATION OF TETRAHYDROCANNABINOLIC ACID

CROSS REFERENCE TO RELATED APPLICATIONS

This application in a continuation of U.S. patent application Ser. No. 16/449,304 filed Jun. 21, 2019, which claims priority to U.S. Provisional Application No. 62/856,837 filed Jun. 4, 2019, the contents of which are incorporated herein in their entirety by reference.

FIELD OF THE INVENTION

This invention relates to methods of mechanically producing highly concentrated tetrahydrocannabinolic acid having a purity exceeding 90%.

BACKGROUND OF THE INVENTION

Cannabinoids are chemicals that influence the CB1 or CB2 receptors in humans, and other mammals. Presently over a hundred cannabinoids have been discovered. There are additional minor receptors in humans that detect various cannabinoids and regulate biological processes.

Cannabinoids include phytocannabinoids derived from plants. The body naturally produces endocannabinoids to regulate bodily processes. Synthetic cannabinoids can be manufactured in a lab setting.

*Cannabis sativa l* is the binomial name for common plant species known as *Cannabis*. It includes marijuana and hemp in their common usage and regulatory definitions. *Cannabis sativa l.* includes more than 500 phytochemicals and compounds, including cannabinoids. Of these compounds, various terpenes are known to have synergistic bio-effect when combined with cannabinoids and consumed. *Cannabis sativa l.*, is known to have the highest concentration of cannabinoids of any plant species.

Some cannabinoids are precursors to other cannabinoids. In particular, tetrahydrocannabinolic acid (THC-A), which is found in abundance in non-hemp varieties of *Cannabis sativa l*, is a precursor to tetrahydrocannabinol (THC). More particularly, decarboxylation of THC-A yields THC. Similarly, cannabidiolic acid (CBD-A) is a precursor to cannabidiol (CBD).

The decarboxylation process of THC is not 100% efficient in that the mass of resulting non-acid form cannabinoid (THC-A) after a decarboxylation reaction is less than the mass of the precursor (THC). Sometimes decarboxylation loses over 10% of the initial cannabinoid mass.

A cost effective way of manufacturing cannabinoids is to extract and isolate these from plant biomass.

Methods of extracting cannabinoids include utilizing solvents such as ethanol, butane, acetone, and lipids. $CO_2$ extraction methods are prevalent where high pressure $CO_2$ extracts oils yielding a high concentration of cannabinoids. Many natural medicine advocates have indicated that high pressures can change the nature of the desirable molecules, and that solvents may leave toxic residue where quality control is not aptly utilized. Further, many of the 500 compounds, particularly terpenes, may degrade or volatilize when heated, or highly processed.

U.S. Pat. No. 9,050,631B2 discloses one way to naturally extract the desired cannabinoids from plant biomass. It involves mechanical tumbling the biomass in a machine using mesh screens having various aperture sizes. This is useful, but not super efficient.

U.S. Pat. No. 9,066,910B2 discloses soaking cannabis flower trimmings in cold or iced water and utilizing mechanical agitation to separate crystallized trichomes from the biomass. The water is filtered using a mesh to separate the trichomes.

In sum, cannabis trichome extraction using cold water and mesh screens has been utilized for many years in the manufacture of hashish and other products. Further improvements in the separation process include the use of air driven and hydraulic mechanisms.

Electronic vaporizers are increasingly popular due to convenience and the desire to mitigate health concerns associated with smoking. One popular electronic vaporizer is a battery powered vaporizer-pen. Importantly, vaporization devices are optimally effective when the viscosity of the cannabis extracts or oils achieve a proper viscosity and consistency.

The cited extraction processes do not fully achieve an extraction product which can be directly vaporized due to the inconsistency in product viscosity. To achieve an optimal viscosity, chemical solvents and thinning agents are utilized as a carrier in order to achieve consistent results and proper viscosities.

Often vaporization devices utilize oil that is decarboxylated (THC), which means that the process has already lost a portion of the mass of the precursor (THC-A). Ideally utilizing THC-A is optimal from a manufacturing standpoint because conversion of an oil containing THC-A to THC through decarboxylation reduces the weight of the oil by 10% or up to 15%. Thus, it is more desirable to manufacture a vaporizable product utilizing a high percentage of THC-A to achieve an optimal product yield.

The difficulty in utilizing THC-A in vaporizable oil is that THC-A tends to crystallize, which normally makes use of THC-A in a vaporizer at high concentrations (above 50%) impractical because the vaporizer device can clog when crystallized cannabinoids are utilized. Thus most vaporizable formulations have very low concentrations of THC-A and high concentrations of THC. Product yield is sacrificed to achieve homogeneity and avoid crystallization.

What is desired is a non-toxic and solvent free method of producing a highly refined tetrahydrocannabinolic acid product. What is also desired is a way of formulating highly pure tetrahydrocannabinolic acid for use in vaporizers, and which does not tend to crystallize.

SUMMARY OF THE INVENTION

The present invention includes a product and method for manufacturing high-purity tetrahydrocannabinolic acid, that does not require chemical solvents or expensive high-performance liquid chromatography (HPLC) equipment.

A method of the invention includes providing *Cannabis sativa l.* biomass, mechanically agitating the biomass in an aqueous bath, such as an ice bath, at a temperature between 32° F. and 35° F. to separate a phytochemical mixture including tetrahydrocannabinolic acid from the biomass. These temperature ranges are effective at ambient pressure i.e. 14-15 PSI.

The method further includes drying the phytochemical mixture. Next the dried phytochemical mixture is used to create a first press product. The first press product is manufactured by pressing the dried phytochemical mixture through a mesh screen with a pressure within the range of 5-120 psi and at a first temperature between 90-120° F. The mesh screen has an average pore size of between 5-25 microns.

The pressure can vary in alternate embodiments of the invention. The temperature is chosen to yield a flowable and translucent product with the consistency of honey to be produced including a significant volume of non-degraded volatile terpenes and tetrahydrocannabinolic acid. The temperatures are low enough to preserve the terpenes.

The first press product having a concentration of between 65-85% of tetrahydrocannabinolic acid on a weight to weight (w:w) basis and between 5-20% terpenes on a weight to weight (w:w) basis. In order to separate the tetrahydrocannabinolic acid from the terpenes, an aging process is used. Accordingly the method includes creating an aged first press product by aging the first press product, the aged first press product being opaque at room temperature. Opaque is relative to the translucent first press product. Opaqueness indicates reactions that bind and crystallize tetrahydrocannabinolic acid molecules, thus inhibiting light to pass readily through the opaque aged first press product.

The method includes creating a second press product by pressing and heating the aged first press product through the same mesh screen a second temperature that is higher than the first temperature to remove a majority of non-cannabinoid lipids and chlorophyll, which are generally deemed undesirable for oral consumption, transdermal delivery, and pulmonary delivery.

After the non-cannabinoid lipids are removed the method includes utilizing the residual product and increasing the temperature to at least 280° F., and preferably 290° F. to melt the tetrahydrocannabinolic acid, which concentrates and flows, and is captured to yield high-purity tetrahydrocannabinolic acid having a 90-99.99% purity. Ideally, increasing the temperature is accomplished slowly, over a ten to fifteen minute period.

The method, according to one aspect of the invention, includes concentrating the first press product tetrahydrocannabinolic acid of at least 65% purity, or more ideally between 75-85% tetrahydrocannabinolic acid on a weight to weight (w:w) basis. This relies upon utilizing trichomes as the starting material. It can be appreciated that biomass can be processed in other ways to achieve such concentrations.

The aged first press product includes crystallized tetrahydrocannabinolic acid that makes the aged first press product opaque, hardened and non-flowable at ambient temperatures. The second press temperature is within the range of 200-220° F. so that the aged first press product can begin to flow during the second press stage. The second press product is pressed for at least ten minutes, and preferably 15 minutes. The temperature is raised from ambient temperatures to the second press temperature over time to enable various undesirable lipids, waxes, chlorophyll, and other elements to melt away, as opposed to vaporizing or otherwise transmuting such elements.

With each pressing stage the temperatures are increased. The second press temperature is higher than the first press temperature. Importantly, since the terpenes are preserved from the first press stage, where a majority of the terpenes are extracted, the subsequent stages do not significantly impact the next yield of terpenes when the process is viewed holistically, and in comparison to other extraction methods. The third pressed product is pressed for at least ten minutes at a third press temperature that rises to above the second press temperature.

According to some data, the boiling point in ° F. of tetrahydrocannabinolic acid is between 308-409 degrees. The melting point is between 167-208° F. It takes time for all of the tetrahydrocannabinolic acid to either boil or melt, so time is required at any temperature within the ranges specified. The present invention optimizes the time and temperatures for optimal yield and manufacturing efficiency.

The third pressed product is pressed at a third press temperature, which reaches beyond the melting point of tetrahydrocannabinolic acid and below the boiling point of tetrahydrocannabinolic acid. Preferably, the third press temperature reaches 290° F. over a ten to fifteen minute period to yield concentrated tetrahydrocannabinolic acid having a purity of at least between 90-95%.

More preferably, the third press temperature reaches 290° F. over a fifteen minute period to yield concentrated tetrahydrocannabinolic acid having a purity of at least 99%.

Concentrated tetrahydrocannabinolic acid readily crystallizes, unless the concentration is limited to less than 50% in an oil solution. Thus terpenes and tetrahydrocannabinolic acid from the first press, and THC (non-acid form) can be mixed to make a vaporizable cannabinoid oil.

Ideally the pure tetrahydrocannabinolic acid from the third press can be decarboxylated to yield sufficient amounts of tetrahydrocannabinol (THC) to dilute the first press product to yield a proper vape oil that will not crystallize and clog a vaporizer device. Thus, the tetrahydrocannabinol is mixed with the terpenes and tetrahydrocannabinolic acid from the first press to make a cannabinoid oil with less than 50% tetrahydrocannabinolic acid on a weight to weight (w:w) basis (less than a 1:1 ratio of THC-A:THC) so that the cannabinoid oil does not crystallize.

Optimally, the concentration of tetrahydrocannabinolic acid is reduced further to assure that age and temperature variations do not cause the vaporizable cannabinoid oil product to crystallize. In one embodiment of a product of the invention the vaporizable cannabinoid oil has a concentration of tetrahydrocannabinolic acid of between 39-40% on a weight to weight (w:w) basis and a terpene concentration of between 5-15%. The THC concentration can be approximately equal to the THC-A concentration.

The step of drying is accomplished a process selected from the group consisting of freeze drying, air drying, vacuum drying, spray drying and combinations thereof.

The mesh screen is preferably made from a material selected from the group consisting of stainless steel, nylon, polyester and aluminum, and combinations thereof.

The step of aging is at least one day in duration. In a preferred embodiment, the step of aging is between 1-14 days in duration.

In an alternate embodiment, the step of aging includes adding a catalyst to the first press product and the duration of the step of aging is less than one day in duration. In this embodiment, the catalyst is dried tetrahydrocannabinolic acid. The catalyst ma alternatively include glass beads to accelerate the step of aging. The glass beads are removed later in the process.

After increasing the temperature to at least 280 degrees to melt the tetrahydrocannabinolic acid in the third press sep, the melted tetrahydrocannabinolic acid is captured to yield a high-purity tetrahydrocannabinolic acid having a 90-99.99% purity.

Biologically active phytochemicals contained within the glandular trichomes of the cannabis plant have typically been extracted using chemical solvents. Furthermore, cannabis extracts used in electronic vaporizers have been crafted using chemical solvents and thinning agents in order to achieve consistent results and proper viscosities.

For vaporization of cannabis oil, the present invention has a viscosity in the range of 2-100 Poise (P), or 200-10,000 centipoise is preferred at 70° F. More preferably, the present invention has a final product viscosity of between 5-100 P.

The invention is created to allow for mechanically separated *cannabis* extracts to be used in a portable electronic vaporizer. It can also be packaged in sealed, glass vials to be smoked or vaporized in a glass concentrate apparatus.

In a preferred embodiment, the method stated here uses no chemical solvents, but merely an agitation in an ice water bath, and filtration, in order to mechanically separate and concentrate the glandular trichomes from the plant biomass.

In one embodiment, the concentrated glandular trichomes undergo post processing after the steps of separating and concentrating the glandular trichomes, which have very high concentrations of cannabinoids, from the plant biomass.

These trichomes are further refined by placing the trichome material in a mesh envelope and applying pressures at 20-140 psi and varying temperatures between 80-300° F. to press the trichome material through 5-25 micron mesh screens to separate volatile phytochemicals, particularly terpenes. The pressure and temperature vary over time according to a customizable and programmed protocol to subsequently extract acid form cannabinoids including CBD-A and THC-A, and others.

In one embodiment a series of mesh screens from 5-25 microns are sequentially utilized. For example, depending on the biomass to be processed, a 25 micron screen can be used, then a 20 micron screen, then a 10 micron screen in each successive pressing step.

First Press

The pressure is varied during the process of separation and concentration to enable a first press, at a first temperature and pressure, to extract a high concentration of volatile terpenes along with only a residual amount of THC-A, such as less than 3% THC-A on a w:w basis and approximately 8-40% volatile terpenes. Most of the THC-A from the trichome material remains in the screen and is thus separated as the volatile terpenes are pressed out of the screen.

Aging

Next, in a sub process, the residual THC-A that flows with the volatile terpenes is further separated from the volatile terpenes by aging the volatile terpene mixture at standard pressure (1 atm) and at a slightly warmer than room temperature (e.g. 80-100° F.) over the course of 10 to 1000 hours.

Optionally, this residual THC-A can be decarboxilated to THC to inhibit crystallization. This THC-A can be later utilized as a by-product, or added to the intermediate vape-product to achieve a desired viscosity prior to packaging into a vaporizer formulation. Utilizing a portion of THC in the vaporizer formulation, while reducing the optimal yield, can be measured to achieve desired cannabinoid content for efficacy, and be measured to achieve a desired viscosity. Utilizing an engineered concentration of THC and THC-A inhibits crystallization of cannabinoids in a vaporizable formulation while optimizing product yield Second Press A second and third press are performed at a relatively higher temperatures and pressure to concentrate THC-A.

The second press produces a concentration of THC-A at second press temperature range of less than the decarboxylation temperature of THC-A. Preferably this temperature is between 250 degrees to 270 degrees to melt the THC-A and to optimize separation and yield of THC-A.

Since the volatile terpenes have already been mostly removed by the first press, very little of the volatile terpenes remain so they are unaffected by the second press. Extracting most of the THC-A after removal of the volatile terpenes in the first press conserves the terpenes while enabling optimization of the solvent-free THC-A extraction. The sequence of pressing steps optimizes the manufacturing process by the cooperation of preserving the volatile terpenes in the first press and preserving the acid form cannabinoids in the second press step.

It can be appreciated that one skilled in the art can add a volatile solvent such as ethanol, or a hydrocarbon, to the mesh envelope to further enhance the yield of THC-A in this step, but a solvent-free extraction is preferred by this inventor.

Third and Subsequent Press Steps

Each of the second and third press concentrate THC-A. The third or subsequent press steps utilizes finer e.g. 5-10 micron screens applied to the product of the second press, for example. The pressure is further increased, and the temperature is maintained, or increased without unnecessarily decarboxylating more than 0.1-3% of the THC-A. The third, or subsequent, pressing steps concentrate the THC-A to over 95%.

It can be appreciated that the third press and subsequent press steps yield less THC-A and other cannabinoids. Thus the temperature can be varied, i.e. increased beyond the point of decarboxylating the THC, CBD or other cannabinoids.

It can be further appreciated that in the case of processing hemp, where CBD yield is desired and THC is sought to be minimized for particular markets, that the process can vary to volatilize THC nearly completely without volatilizing the CBD. This preserves the CBD and converts the THC to CBD. This can yield a nearly zero THC product.

In one embodiment a first pressure of 20-50 PSI and a first temperature of between 80-120° F. is used initially to press the trichome 5-25 microns to yield first press material having a yield of 8-40% terpenes. The relatively low temperature preserves volatile terpenes, which are extracted and preserved at between 70-120° F. This preservation step also enables natural crystallization and concentration of THC-A.

The vaporizable oil product is a mixture of the volatile terpenes extracted in the first press, the THC-A separated in the second step, and the addition of sufficient THC to achieve a desired viscosity. The concentration of CBD-A is less than 55% on a w:w basis to inhibit crystallization, and more preferably is approximately 30-45% to both optimize product yield and to inhibit crystallization. Most preferably the THC-A concentration is between 39-41% to assure that crystallization of the THC-A will not occur.

The process of the present invention thus yields a vaporizable *cannabis* oil having between 30-41% THC-A, or optimally, between 39-41% THC-A.

The viscosity is optimized to enable nebulization in commercially vaporizer devices, such as multiple use vaporizer pens.

Once the volatile phytochemicals have been filtered under pressure, they begin to separate naturally into a high viscosity fraction and low viscosity fractions. This is an aging process.

In the past, High Pressure Liquid Chromatography (HPLC), or regulated distillation methods, has been relied upon to achieve fractionation of materials into isolated components. HPLC machines are very expensive to purchase and operate. The present invention enables an acceptable degree of fractionization of cannabinoids without the need for HPLC.

These fractions are collected and mixed. Preferably, the total terpene concentration is between 5-15% of the product on a weight to weight basis (w:w) in order for the proper viscosity to be achieved the enables use in a vaporizer. The terpenes are contained in the high viscosity fraction in concentrations between 5-30%. Once the proper viscosity, and terpene and cannabinoid ratios are determined through testing, the formulation can be used in an electronic vaporizer.

DETAILED DESCRIPTION

Figure 1:
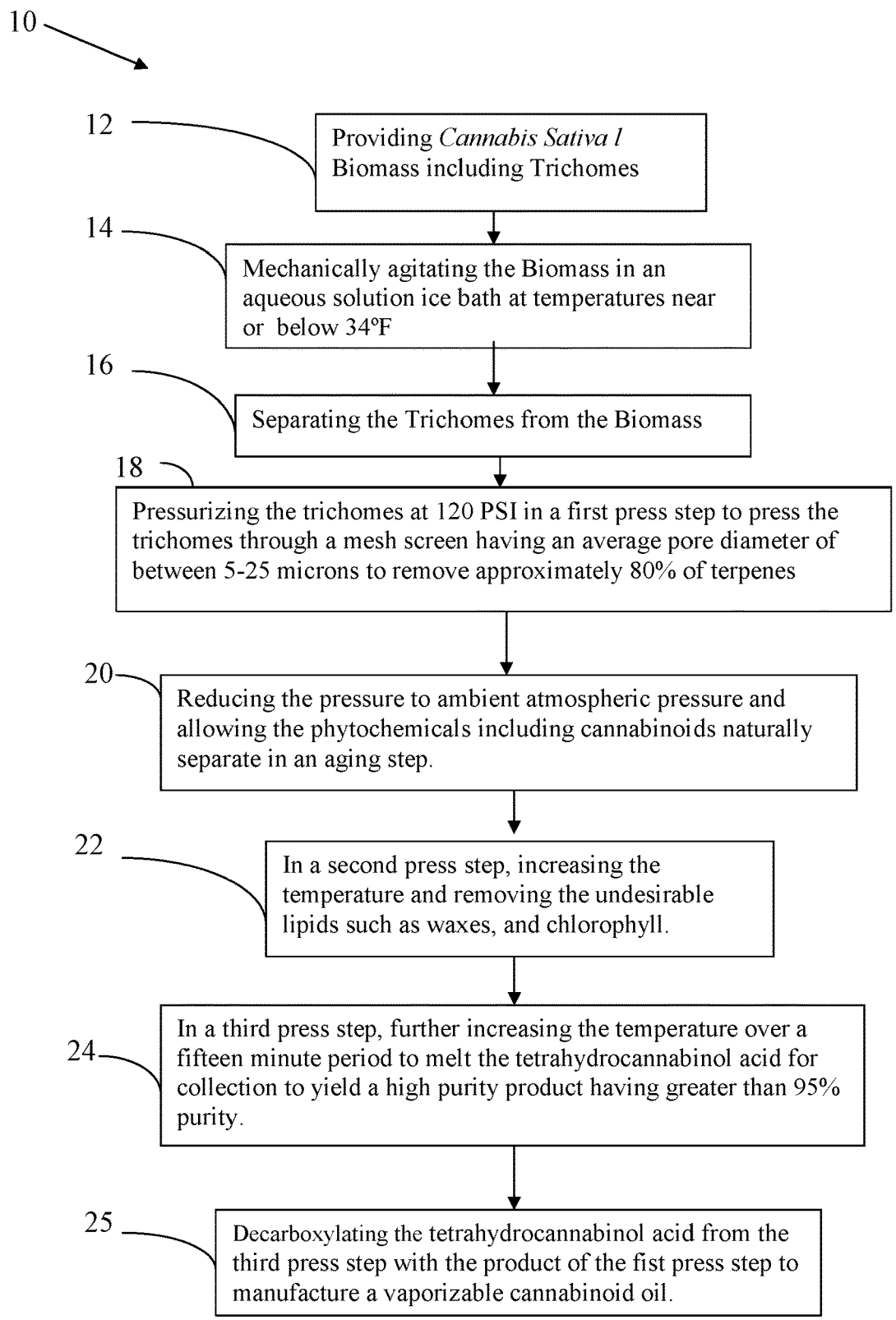
FIG. 1 is a flowchart of a method in accordance with the present invention.

FIG. 1 is a method generally designated with the reference numeral 10. The method 10 includes the step 12 of providing *Cannabis sativa l* biomass including trichomes. The biomass can be hemp derived, or non-hemp derived. Non-hemp derived trichomes are derived from *Cannabis sativa l* having biomass with no more than 0.3% THC on a weight to weight w:w basis.

The method includes the step 14 of mechanically agitating the biomass in a vessel including an aqueous solution ice bath at temperatures near or below 34° C. "Near" in this context and the context of usage in this document is a range within +/−10% of the stated numerical range. The step 16 relies on the mechanical agitation step 14 to separate the trichomes from the biomass. The trichomes separate from the aqueous solution and typically settle.

Agitation in the ice bath increases the efficiency of the removal of the trichomes from the cannabis material. The cold temperatures help solidify the glandular trichomes, allowing them to break free from the biomass. The trichomes are denser than the remaining biomass and the aqueous solution so they sink to the bottom of the vessel during agitation. The trichomes are collected, removed from the aqueous solution in the form of a resin and dried to form a dry resin.

The drying process involves sublimation using a freeze dryer. A freeze dryer is able to freeze the water molecules contained within the resin and pass directly to a gas state by the use of decreased pressure, which frees the water from the concentrate. There are at least forty known terpenes. Test results of material after the drying process are expressed in Table 1 which were taken from a sample having approximately 8% terpene content. The terpene content and concentration depend on the variety of *Cannabis sativa l*, and growing conditions.

TABLE 1

| Terpene Content | | |
| --- | --- | --- |
| Terpene | % Weight | Mg/g |
| α-Pinene | 0.21% | 2.10 |
| Camphene | 0.06% | 0.60 |
| Myrcene | 0.85% | 8.50 |
| β-Pinene | 0.41% | 4.10 |
| 3-Carene | <0.01% | ND |
| α-Terpinene | <0.01% | ND |
| Limonene | 3.02% | 30.20 |
| p-Cymene | ND | ND |
| Ocimene | <0.01% | ND |
| Eucalyptol | ND | ND |
| Gamma-Terpinene | ND | ND |
| Terpinolene | 0.04% | 0.40 |
| Linalool | 0.72% | 7.20 |
| Isopulegol | ND | ND |
| Geraniol | 0.02% | 0.20 |
| Caryophyllene | 1.75% | 17.50 |
| Humulene | 0.44% | 4.40 |
| Nerolidol | 0.15% | 1.50 |
| Guaiol | <0.01% | ND |
| Caryophyllene-Oxide | 0.02% | 0.20 |
| α-Bisabolol | 0.35% | 3.50 |
| Total | 8.04% | 80.50 |

First Press

Once the resins are dried they must be further refined using high pressure a press. A low micron mesh screen is wrapped securely around the raw, dried resin, and pressed at high pressures to force only the volatile compounds through the mesh, leaving behind plant material or other contaminated. Once the resin has went through an initial refinement, it will begin to separate naturally into two layers: one that contains high concentrations of THC-A and low viscosity lipids and waxes, and one that contains a high terpene concentration and highly viscous lipids, waxes and uncrystallized cannabinoids.

In one embodiment the rosin press has a capability of utilizing up to 15,300 pounds of force on a 30 square inch plate to press the resin. This is approximately 510 lbs per square inch. Preferably, to maintain the integrity of the cannabinoids, terpenes, and other constituents, the pressure is regulated between ambient pressures and 200 lbs of pressure (PSI). More preferably, the pressure is between 20-140 PSI.

The step 18 pressurizes the vessel at pressures of between 20 PSI to 120 PSI. The pressure forces the trichomes through a stainless steel mesh screen having an average pore diameter of 5-25 microns without significant degradation of the resin. The temperature is regulated between 110° F.-120° F. +/−10%.

It can be further appreciated that additional filtration, centrifugation, evaporation, or combinations thereof, can effectuate this collection step to optimize yield of the resin when sequenced in combination with pressurization.

The method includes the step 20 of reducing the pressure of the vessel to ambient atmospheric pressure. Allowing the pressed material to stand enables phytochemicals in the pressed material, including cannabinoids, to naturally separate into a high viscosity fraction and a low viscosity fraction. The step 22 ends the step 20 when a pre-determined target a total terpene concentration of between 5-15% is achieved in the low viscosity fraction. The high viscosity fraction has a relatively higher viscosity than the total terpene concentration than the low viscosity fraction. These fractions are combined in optimal ratios to achieve a desired viscosity for use in a vaporizer device. In an alternate embodiment, the fractions are mixed to pre-process the material for a third press step.

The step 24 is a third press step including further increasing the temperature over a fifteen minute period to melt the tetrahydrocannabinol acid for collection to yield a high purity product having greater than 95% purity.

The step 25 achieves a cannabinoid-rich oil product that is manufactured without solvents and has a desired viscosity for pulmonary delivery through a vaporizer. This product can be packaged and utilized in a vaporizer by a subject or user. In particular, the step 25 includes decarboxylating a portion of the high purity product of the step 24 and mixing it with the product of the first press step 18 so that the concentration of tetrahydrocannibidiolic acid is diluted by the THC to inhibit crystallization in the vaporizable cannabinoid product.

Figure 2:
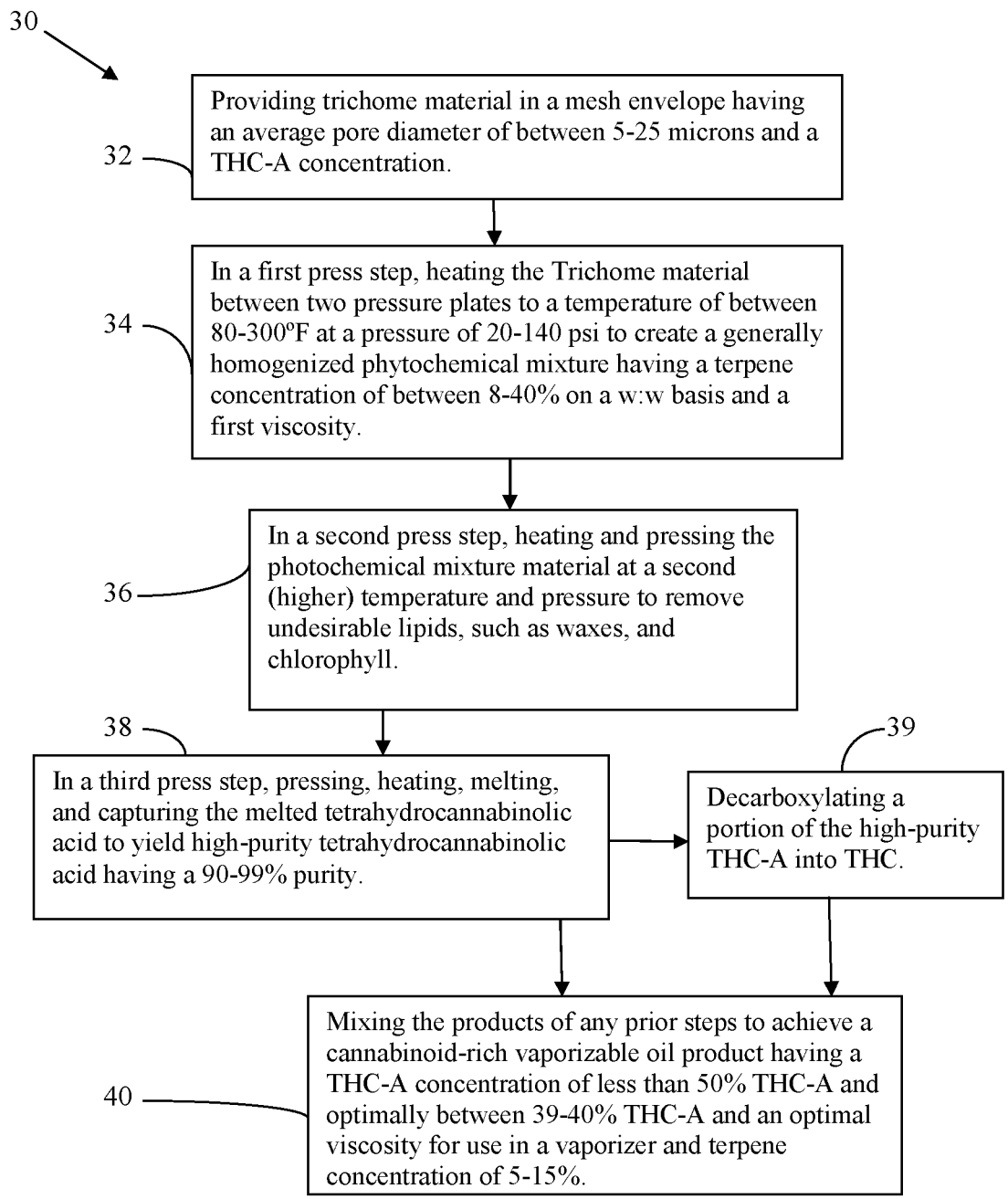
FIG. 2 is a flowchart of a method in accordance with the present invention.

FIG. 2 is a flow chart of a method generally designated with the reference numeral 30. The method 30 includes the step 32 of providing trichome material in a mesh envelope having an average pore diameter of between 5-25 microns and a THC-A concentration.

The step 34 includes a first press step, heating the Trichome material between two pressure plates to a temperature of between 80-300° F. at a pressure of 20-140 psi to extract volatile terpenes into a terpene mixture having a terpene concentration of between 8-40% on a w:w basis and a first viscosity.

The step 36 includes a second press step, heating and pressing the trichome material at a second (higher) temperature and pressure, to remove undesirable lipids including waxes, and chlorophyll.

The step 38 includes a third press step at the third temperature, higher than the second temperature, to in a third press step, pressing, heating, melting, and capturing the melted tetrahydrocannabinolic acid to yield high-purity tetrahydrocannabinolic acid having a 90-99.99% purity.

The step 39 includes converting, by decarboxylation, a portion of the tetrahydrocannabinolic acid to THC. Ideally the pure tetrahydrocannabinolic acid having a 90-99.99% purity is used so that volatile terpenes are not volatilized and wasted. A desired amount of THC is then added in step 40 to optimize a cannabinoid vaporizable product which will not crystallize due to the optimal balance of THC, THC-A and terpenes.

The step 40 mixes the products of any prior steps to achieve a cannabinoid-rich vaporizable oil product having a THC-A concentration of less than 50% THC-A and optimally between 39-40% THC-A and an optimal viscosity for use in a vaporizer and terpene concentration of 5-15%.

What is claimed is:

1. A method for manufacturing high-purity vaporizable cannabinoid oil product including tetrahydrocannabinolic acid, comprising:
   providing *Cannabis sativa l.* biomass;
   mechanically agitating the biomass in an aqueous bath at a temperature between 32° F. and 35° F. to separate a phytochemical mixture including tetrahydrocannabinolic acid from the biomass;
   drying the phytochemical mixture;
   creating a first press product by pressing the dried phytochemical mixture through a first mesh screen at a pressure within the range of 5-120 psi and at a first temperature between 90-120° F., the first press product having a concentration of between 65-85% tetrahydrocannabinolic acid on a weight to weight (w:w) basis and between 5-20% terpenes on a weight to weight (w:w) basis;
   creating an aged first press product by aging the first press product, the aged first press product being opaque at room temperature;
   creating a second press product by heating the aged first press product and pressing the heated aged first product through a second mesh screen a second temperature that is higher than the first temperature to remove a majority of non-cannabinoid lipids and chlorophyll;
   increasing the temperature to 290° F. to melt the tetrahydrocannabinolic acid;
   capturing the melted tetrahydrocannabinolic acid to yield high-purity tetrahydrocannabinolic acid having a 90-99.99% purity;
   decarboxylating a portion of the tetrahydrocannabinolic acid to yield tetrahydrocannabinol;
   preparing a vaporizable oil product that is a mixture of the volatile terpenes of the first press product, the tetrahydrocannabinolic acid of the second press product, and the tetrahydrocannabinol so that the vaporizable oil has a THC-A concentration of between 30-41% and a viscosity suitable to enable the vaporizable cannabinoid oil product to be used in a vaporizer device.

2. The method as set forth in claim 1, wherein the second press temperature is within the range of 200-220° F.

3. The method as set forth in claim 2, wherein the step of creating the second press product includes pressing the heated aged first product for at least ten minutes.

4. The method as set forth in claim 1, wherein a portion of the tetrahydrocannabinolic acid is decarboxylated to yield tetrahydrocannabinol, and the tetrahydrocannabinol is mixed with the terpenes and tetrahydrocannabinolic acid from the first press to inhibit crystallization of the vaporizable cannabinoid oil product.

5. The method as set forth in claim 1, wherein the step of drying is accomplished a process selected from the group consisting of freeze drying, air drying, vacuum drying, spray drying and combinations thereof.

6. The method as set forth in claim 1, wherein the vaporizable cannabinoid oil product has a concentration of tetrahydrocannabinolic acid of between 39-40% on a weight to weight (w:w) basis.

7. The method as set forth in claim 6, wherein the vaporizable cannabinoid oil product has a terpene concentration of between 5-15%.

8. The method as set forth in claim 1, wherein at least one of the first or second mesh screens has a pore size of between 5-25 microns.

9. The method as set forth in claim 8, wherein at least one of the first or second mesh screens is made from a material selected from the group consisting of stainless steel, nylon, polyester and aluminum, and combinations thereof.

10. The method as set forth in claim 1, wherein the step of aging is at least one day in duration.

11. The method as set forth in claim 10, wherein the step of aging is between 1-14 days in duration.

12. The method as set forth in claim 1, wherein the step of aging includes adding a catalyst to the first press product and the duration of the step of aging is less than one day in duration.

13. The method as set forth in claim 11, wherein the step of aging includes adding a catalyst to the first press product and the duration of the step of aging is less than one day in duration.

14. The method as set forth in claim 13, wherein the catalyst is dried tetrahydrocannabinolic acid.

15. The method as set forth in claim 13, wherein the catalyst includes glass beads to accelerate the step of aging.

* * * * *